(12) United States Patent
Kapoor et al.

(10) Patent No.: US 11,432,879 B2
(45) Date of Patent: Sep. 6, 2022

(54) METHOD AND APPARATUS FOR WIDE AREA MULTI-BODY 6D POSE TRACKING SYSTEM

(71) Applicant: Siemens Healthcare GmbH, Erlangen (DE)

(72) Inventors: Ankur Kapoor, Plainsboro, NJ (US); Ali Kamen, Skillman, NJ (US); Gianluca Paladini, Skillman, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 280 days.

(21) Appl. No.: 16/104,995

(22) Filed: Aug. 20, 2018

(65) Prior Publication Data

US 2019/0053858 A1 Feb. 21, 2019

Related U.S. Application Data

(60) Provisional application No. 62/547,238, filed on Aug. 18, 2017.

(51) Int. Cl.
*A61B 34/20* (2016.01)
*G01B 11/00* (2006.01)
(Continued)

(52) U.S. Cl.
CPC .............. *A61B 34/20* (2016.02); *A61B 8/12* (2013.01); *A61B 8/4254* (2013.01);
(Continued)

(58) Field of Classification Search
CPC ......... A61B 34/20; A61B 8/12; A61B 8/4263; A61B 8/4254; A61B 2090/378;
(Continued)

(56) References Cited

U.S. PATENT DOCUMENTS 6,484,131 B1 11/2002 Amoral-Moriya et al.
6,535,114 B1 3/2003 Suzuki et al.
(Continued)

OTHER PUBLICATIONS

NDI Measurement Sciences, Optotrak Certus, https://www.ndigital.com/msci/products/optotrak-certus/; retrieved on Sep. 14, 2018; 4 pgs.

(Continued)

*Primary Examiner* — Joseph M Santos Rodriguez
*Assistant Examiner* — Kaitlyn E Sebastian

(57) ABSTRACT

An apparatus and method for tracking the position and orientation of one or more objects in three dimensional space is disclosed. One or more tracked sensor units are each connected with a respective object. Each tracked sensor unit includes one or more light sources and an inertial measurement unit. One or more position sensitive detector tracking devices track the position of the tracked sensor units. Each position sensitive detector tracking device includes a plurality of position sensitive detector sensors combined with optical lenses that focus light from a larger field of view onto each position sensitive detector sensor. The position and orientation of each object in three-dimensional space is calculated from the output of the inertial measurement unit of the respective tracked sensor unit and the output of the one or more position sensitive detector tracking devices in response to light emitted from the one or more light sources of the respective tracked sensor unit.

19 Claims, 10 Drawing Sheets

(51) Int. Cl.
*G01C 21/10* (2006.01)
*A61B 8/00* (2006.01)
*A61B 8/12* (2006.01)
*A61B 90/00* (2016.01)

(52) U.S. Cl.
CPC .......... *A61B 8/4263* (2013.01); *G01B 11/002* (2013.01); *G01C 21/10* (2013.01); *A61B 2034/2048* (2016.02); *A61B 2034/2055* (2016.02); *A61B 2090/378* (2016.02)

(58) Field of Classification Search
CPC .... A61B 2034/2048; A61B 2034/2055; G01B 11/002; G01C 21/10
See application file for complete search history.

(56) References Cited

U.S. PATENT DOCUMENTS

| | | | |
|---|---|---|---|
| 8,384,912 B2 | 2/2013 | Charny et al. | |
| 8,593,647 B2 | 11/2013 | Charny et al. | |
| 9,087,379 B2 | 7/2015 | Wang et al. | |
| 9,142,022 B2 | 9/2015 | Melax et al. | |
| 9,325,974 B2* | 4/2016 | Hebert | G06T 7/75 |
| 9,349,048 B2 | 5/2016 | Kwak et al. | |
| 9,524,434 B2 | 12/2016 | Gee et al. | |
| 9,816,813 B2* | 11/2017 | Lettau | G01C 15/002 |
| 10,049,277 B2 | 8/2018 | Kim et al. | |
| 2013/0003042 A1* | 1/2013 | Sogard | G01B 5/012 356/23 |
| 2013/0128054 A1* | 5/2013 | Densham | G03B 21/53 348/169 |
| 2013/0329439 A1* | 12/2013 | Hellkamp | A42B 3/044 362/464 |
| 2016/0059044 A1* | 3/2016 | Gertner | A61B 18/1492 601/2 |
| 2017/0108528 A1* | 4/2017 | Atlas | G01S 3/783 |
| 2017/0122729 A1* | 5/2017 | Tarbutton | G01B 11/002 |
| 2017/0292827 A1 | 10/2017 | Haverkamp | |
| 2018/0049809 A1* | 2/2018 | Marti | A61B 90/37 |

OTHER PUBLICATIONS

ART Advanced Realtime Tracking; https://ar-tracking.com; retrieved on Sep. 14, 2018; 3 pgs.
NDI Measurement Sciences, 3D Guidance driveBAY and trakSTAR, https://www.ndigital.com/msci/products/drivebay-trakstar/; retrieved on Sep. 14, 2018, 8 pgs.
Adafruit, Triple-axis Accelerometer+Magnetometer (Compass) Board,https://www.adafruit.com/product/1120?gclid=CMeO0JT7htQCFdKLswodoxUAgw, retreived on Sep. 14, 2018, 4 pgs.
Woltring, Herman J., "Single-and dual-axis lateral photodectors of rectangular shape", IEEE Transactions on Electron Devices 22.8, 1975; pp. 581-590.
Wang et al., "The Linearity and Sensitivity of Lateral Effect Position Sensitive Devices—An Improved Geometry", IEEE Transactions on Electron Devices, 36.11, 1989, pp. 2475-2480.
Cui et al., "Linearity Indices and Linearity Improvement of 2-D Tetralateral Position-Sensitive Detector", vol. 57, No. 9, Sep. 2010, pp. 2310-2316.
Bouguet, Jean-Yves, "Visual methods for three-dimensional modeling" 1999; Pasadena, CA: California Institute of Technology; Chapter 3.

\* cited by examiner

Figure 4: High efficiency Laser based light emitting diode

METHOD AND APPARATUS FOR WIDE AREA MULTI-BODY 6D POSE TRACKING SYSTEM

This application claims the benefit of U.S. Provisional Application No. 62/547,238, filed Aug. 18, 2017, the disclosure of which is herein incorporated by reference in its entirety.

BACKGROUND OF THE INVENTION

The present invention relates to tracking position and orientation of objects within a defined space, and more particularly to wide area six-dimensional (6D) pose tracking of objects such as ultrasound probes and medical devices.

Pose tracking refers to tracking the position and orientation measurements of rigid bodies that move in a defined space. The total number of measurements is six, which includes three positional and three orientation values in three-dimensional (3D) space. Tracking the position and orientation of objects within a large area is required in a variety of applications from medical interventional navigation to gaming.

BRIEF SUMMARY OF THE INVENTION

The present invention provides an apparatus and method for tracking a position and orientation of target objects over a wide area.

In an embodiment of the present invention, an apparatus for tracking a position and orientation in three-dimensional space of one or more objects comprises: one or more tracked sensor units, each tracked sensor unit connected with a respective one of the one or more objects and comprising one or more light sources and an inertial measurement unit; one or more position sensitive detector tracking devices, each position sensitive detector tracking device comprising a plurality of position sensitive detector sensors combined with optical lenses that focus light from a field of view onto each position sensitive detector sensor; and a processing unit configured to calculate the position and orientation of each of the one or more objects in three-dimensional space from output of the inertial measurement unit of the respective tracked sensor unit and output of the one or more position sensitive detector tracking devices in response to light emitted from the one or more light sources of the respective tracked sensor unit.

In an embodiment, in response to light emitted from a light source of a tracked sensor unit being focused onto each of the plurality of position sensitive detector sensors of a position sensitive detector tracking device, each of the plurality of position sensitive detectors measures a 2D location of the light source of the tracked sensor unit with respect to that position sensitive detector, and the processing unit is configured to triangulate a 3D position of the light source of the tracked sensor based on the 2D locations measured by the plurality of position sensitive detectors.

In an embodiment, each position sensitive detector tracking device further comprises a local inertial measurement unit, and the processing unit is configured to calculate a 3D orientation of each of the one or more objects with respect to each position sensitive detector tracking unit based on orientation measurements from the inertial measurement unit of the respective tracked measurement unit and orientation measurements from the local inertial measurement unit of the position sensitive detector tracking device.

In an embodiment, the one or more light sources of each tracked sensor unit comprise one or more light emitting diodes.

In an embodiment, the one or more light sources of each tracked sensor unit comprises a plurality of light emitting diodes arranged around an axis of the respective object to which the tracker sensor unit is connected.

In an embodiment, each tracked sensor unit further comprises a respective processing unit configured to control activation of the one or more light sources and to transmit orientations measurements output by the inertial measurement unit to the processing unit that calculates the position and orientation of the one or more objects.

In an embodiment, the processing unit comprises a respective processing unit embedded in each of the one or more position sensitive detector tracking devices, wherein each respective processing unit embedded in a position sensitive detector tracking device is configured to calculate the position and orientation of each of the one or more objects in three-dimensional space with respect to that position sensitive detector tracking device from the output of the inertial measurement unit of each tracked sensor unit and output of the plurality of position sensitive detector sensors in response to light emitted from the one or more light sources of each tracked sensor unit.

In an embodiment, the inertial measurement unit comprises one or more of an accelerometer, a gyroscope, or a magnetometer.

In an embodiment, at least one of the one or more objects is a handheld ultrasound transducer, the one or more light sources of the tracked sensor device connected the handheld ultrasound transducer comprises a plurality of light emitting diodes arranged in a pattern around the handheld ultrasound transducer, and the one or more position sensitive detector tracking devices each comprise optical lenses of a fixed focal length and a filter configured to isolate information from a range of frequencies of the light emitting diodes.

In an embodiment, the handheld ultrasound transducer comprises a laparoscope ultrasound transducer, and wherein a first set of inertial measurement units are positioned in a first portion of the laparoscope with an ultrasound array, the first portion being rotatable relative to a fixed second portion of the laparoscope, and a second set of inertial measurement units are positioned on the fixed second portion along with the plurality of light emitting diodes.

In an embodiment, at least one of the one or more objects is a medical instrument, the one or more light sources of the tracked sensor device connected to the medical instrument comprises a plurality of light emitting diodes arranged in a pattern around the medical instrument, and with the one or more position sensitive detector tracking devices each comprise an optical lenses of a fixed focal length and a filter configured to isolate information from a range of frequencies of the light emitting diodes.

In an embodiment, the medical instrument comprises a first portion that is rotatable or articulated relative to a fixed second portion of the instrument, and wherein the tracked sensor device connected to the medical instrument comprises a first set of inertial measurement units positioned in the first portion of the medical instrument and a second set of inertial measurement units positioned in the second portion of the medical instrument along with the plurality of light emitting diodes.

In an embodiment, the one or more position sensitive detector tracking devices comprise a plurality of position sensitive detector tracking devices, each position sensitive detector tracking device configured to track the position of each of the one or more objects in a respective coordinate system associated with that position sensitive detector tracking device.

In an embodiment, the one or more position sensitive detector tracking devices comprise a network of position sensitive detector tracking devices each with a tracked sensor unit attached thereto, such that each position sensitive detector tracking device in the network tracks positions of the one or more objects and positions of other position sensitive detector tracking devices in the network.

In another embodiment of the present invention, a method for tracking a position and orientation of one or more objects in three-dimensional space comprises: receiving orientation measurements for each object acquired from an inertial measurement unit of a tracked sensor unit attached that object; acquiring, from each of a plurality of position sensitive detectors, a respective 2D location measurement of at least one light source of the tracked sensor unit attached to each object in response to light from the at least one light source being focused onto the plurality of position sensitive detectors by respective optical lenses; triangulating a 3D position of each object from the respective 2D location measurements acquired from the plurality of position sensitive detectors; and calculating a six-dimensional pose of each object including 3D position and 3D orientation of the object based on the triangulated 3D position and the received orientation measurements.

In an embodiment, triangulating a 3D position of each object from the respective 2D location measurements acquired from the plurality of position sensitive detectors comprises: triangulating a 3D position of each object with respect to a reference one of the plurality of position sensitive detectors from the respective 2D location measurements acquired from the plurality of position sensitive detectors.

In an embodiment, the method further comprises acquiring local orientation measurements of the reference one of the plurality of position detectors from a local inertial measurement unit, and calculating a six-dimensional pose of each object including 3D position and 3D orientation of the object based on the triangulated 3D position and the received orientation measurements comprises: calculating the 3D orientation of each object with respect to the reference one of the plurality of position sensitive detectors based on the received orientation measurements of each object and the local orientation measurements of the reference one of the plurality of position detectors.

In an embodiment, at least one light source of the tracked sensor unit attached to each object comprises a plurality of light emitting diodes arranged around an axis of the object, and the method further comprises: controlling a subset of the plurality of the light emitting diodes that are facing the plurality of position sensitive detectors to turn on, wherein the subset of the plurality of the light emitting diodes that are facing the plurality of position sensitive detectors is determined based on the orientation measurements of the object acquired from the inertial measurement unit.

In an embodiment, acquiring, from each of a plurality of position sensitive detectors, a respective 2D location measurement of at least one light source of the tracked sensor unit attached to each object in response to light from the at least one light source being focused onto the plurality of position sensitive detectors by respective optical lenses comprises: tracking an intensity of light on the plurality of position sensitive detectors; and acquiring, from the plurality of position sensitive detectors, the respective 2D location measurements in response to the intensity of the light on the plurality of position sensitive detectors being greater than a threshold.

In an embodiment, the method further comprises: transmitting an acknowledgment to the tracked sensor unit attached to each object in response to acquiring, from the plurality of position sensitive detectors, the respective 2D location measurements of at least one light source of the tracked sensor unit attached to each object.

In another embodiment of the present invention, an apparatus for tracking position and orientation of an ultrasound probe in 3D space, comprises: a tracked sensor unit attached to the ultrasound probe, the tracked sensor unit comprising a plurality of light emitting diodes arranged in a pattern around an axis of the ultrasound probe and an inertial measurement unit; and a position sensitive detector tracking device comprising a plurality of position sensitive detector sensors combined with optical lenses that focus light emitted from one or more of the plurality of light emitting diodes of the tracked sensor unit onto each position sensitive detector sensor, and a processing unit configured to calculate the position and orientation of the ultrasound probe in three-dimensional space from output of the inertial measurement unit of the tracked sensor unit attached to the ultrasound probe and output of the plurality of position sensitive detector sensors in response to light emitted from at least one of the plurality of light emitting diodes of the tracked sensor unit being focused on the each position sensitive detector sensor by the optical lenses.

These and other advantages of the invention will be apparent to those of ordinary skill in the art by reference to the following detailed description and the accompanying drawings.

DETAILED DESCRIPTION

The present invention relates to an apparatus and method for tracking position and orientation of one or more objects over a wide area.

Tracking position and orientation of objects within a large area is important in a variety of applications ranging from medical interventional navigation to gaming. There are three main categories of contactless technologies that are used for tracking the pose (position and orientation) of an object: 1) optical/acoustic triangulation based on passive or active markers; 2) magnetic sensing and pose estimation; and 3) inertia based systems based on double integration of a set of accelerometers. Each of these technologies has pros and cons including line of sight requirements, bulky/wired sensors, magnetic interference, and cost. Embodiments of the present invention provide a low cost and accurate 6D pose (i.e., 3D position and 3D orientation) tracking system. Embodiments of the present invention provide a system and method that tracks position and orientation of one or more objects accurately, in real time, with low-latency, over a large area (as compared to existing techniques), without being subject to magnetic interference. In addition, embodiments of the present invention require few computational resources and can be implemented very inexpensively.

Existing tracking systems suffer from low positional accuracy, jitter, and drift. Such tracking systems are based on charge couple device (CCD) cameras, depth cameras, structured light, time-of-flight, or magnetic tracking technologies that are incapable of achieving sub-millimeter and sub-degree accuracy. Such tracking systems typically have positional accuracy measured in centimeters. Embodiments of the present invention uniquely integrate Position Sensitive Detector (PSD) sensors (originally designed for aligning laser optics equipment with extreme accuracy) with optics in front of each PSD, to focus light from a larger field of view onto the PSD. In addition, tracked sensor units comprising light-emitting diodes being positionally tracked by the PSD sensors are paired with inertial measurement unit (IMU) sensors capable of providing orientation information, thus combined into a system that can track both position and orientation with a high degree of accuracy. In addition, embodiments of the present invention provide a tracking system that is resilient to jitter noise and drift and is far less expensive than costly magnetic tracking systems, which are also less accurate.

Figure 1:
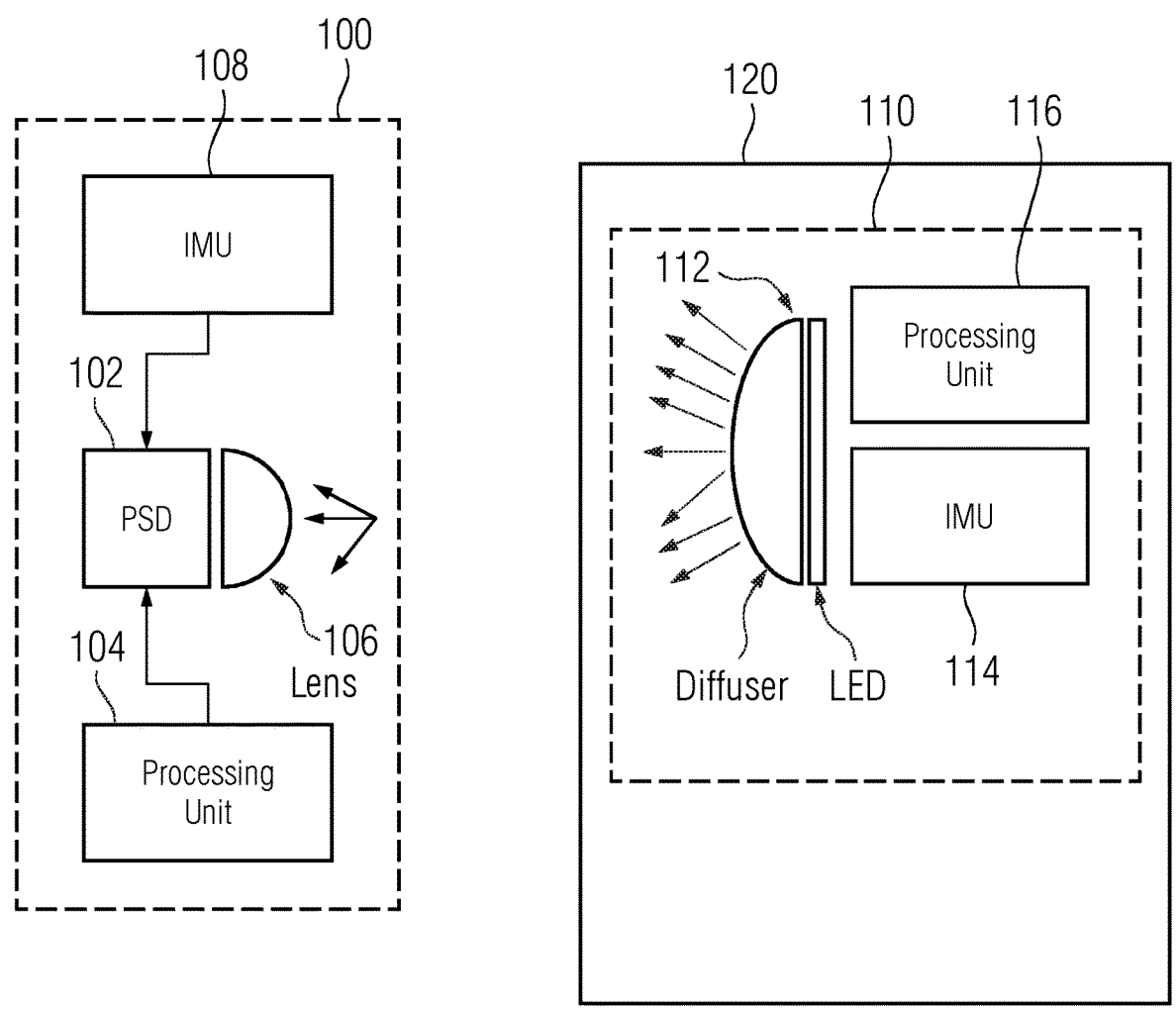
FIG. 1 illustrates a system for tracking position and orientation of a target object according to an embodiment of the present invention.

FIG. 1 illustrates a system for tracking position and orientation of a target object according to an embodiment of the present invention. As shown in FIG. 1, the system includes a PSD tracking device 100 and a tracked sensor unit 110 attached to an object 120 to be tracked. In an exemplary embodiment, the object 120 to be tracked can be an ultrasound probe or other medical tool, but the present invention is not limited thereto. The tracked sensor unit 110 combines a light spot source 112, such as an active light emitting diode (LED) equipped with a diffuser that spreads the light from the LED, with an inertial measurement unit (IMU) 114. The tracked sensor unit 110 includes a processing unit 116 that transmits accurate angular orientation information detected by the IMU, either wirelessly (powered by a miniature battery) or through wires, to a receiving processing unit 104, which can be provided in the PSD tracking device 100 or a separate computer device. The PSD tracking device 100 tracks one or more light spots (from the light spot source of the tracked sensor unit 110) using a pair of Position Sensitive Detectors (PSDs) 102 mounted therein, which are able to accurately detect the location of such light spots and transmit the locations to a processing unit 104 where the locations can be triangulated into three-dimensional positions and track within a wide area of space. A respective lens 106 is provided in front of the each PSD 102 to focus light from the light source 112 of the tracked sensor unit 110 onto the PSD 102. The PSD tracking device 100 can also be equipped with an IMU 108 that provides orientation measurements of the PSD tracking device 100. The fusion of sensors in the tracked sensor unit 110 and the PSD tracking device 100 ensures that position is measured by the PSDs 102 in the PSD tracking device 100 while orientation is measured by the IMUs 114 in each tracked sensor unit 110 being tracked. The components used to implement the system of FIG. 1, which will be described in greater detail below, are low-cost, high-accuracy, and can perform in real-time with low latency.

In various embodiments of the present invention, the light spot source 112 in the tracked sensor unit 110 can be active or passive. For example, in the embodiment shown in FIG. 1, the light spot source can be an active LED strobing at a particular frequency so that the PDUs 102 in the PSD tracking device 100 can discern between different light spots belonging to different tracked sensor units provided on different objects to be tracked. In another embodiment, the light spot source can be a passive marker that reflects light, thereby not needing power. In this case, the use of markers with different retroreflective properties can be used to discern between multiple light spots belonging to different tracked sensor units.

In various embodiments of the present invention, the tracked sensor units 110 can transmit data wirelessly or via a wire. In an embodiment in which the tracked sensor unite 110 is connected to a wire, the wire can be used to transmit orientation information from the IMU sensor 114. In an embodiment in which the tracked sensor unit 110 is wireless, a processing unit 116 capable of wireless connectivity such as Bluetooth can be employed to transmit the IMU data. In an embodiment in which the tracked sensor unit 110 is wireless but does not have wireless network connectivity, the LED light can be employed to communicate IMU data to the PSDs 102 in the PSD tracking device 100 by modulating frequency and/or intensity.

In various embodiments of the present invention, various methods can be employed to supply power to the tracked sensor unit 110. In an embodiment in which the tracked sensor unit 110 is connected to a wire, the wire can carry power for the LED and IMU 114 in the tracked sensor unit 110. In an embodiment in which the tracked sensor unit 110 is wireless, a miniature battery can be employed to supply power to the LED, IMU 114, and processing unit 116 in the tracked sensor unit 110. In an embodiment in which the tracked sensor unit 110 is wireless and battery-less, power to the tracked sensor unit 110 can be transferred wirelessly using existing radio-frequency identification (RFID) technology, such as battery-free RFID LED.

The processing unit that receives and processes sensor information can be housed in the PSD tracking device 100 itself or it can be in a separate computer device, or a combination of both. For example, triangulation of the PSD locations can be computed by the processing unit 104 in the PSD tracking device 100 or the locations detected by the PSDs can be transmitted to a separate computer device and triangulated there. Tracked sensor units 110 can transmit orientation information either to the PSD tracking device 100 (which may then re-transmit the orientation information to a separate computer together with the position information), or the orientation information can be transmitted to a separate computer, either wirelessly or through wires, and the computer can combine the orientation information with position information received from the PSD tracking device 100. The PSD tracking device 100 can communicate with a separate processing computer via a wire or wireless connection.

The position and orientation of the tracked sensor unit 110 being detected by the PSD tracking device 100 and tracked sensor unit 110 is the relative position and orientation of the tracked sensor unit 110 (and the object 120) with respect to the PSD tracking device 100. Accordingly, in an embodiment of the present invention, the detected position and orientation can be converted to an absolute frame of reference. In one embodiment, the PSD tracking device 100 can be calibrated beforehand at a known position and remain stationary. Alternatively, in another embodiment, the PSD tracking device 100 can be moveable, and one or more specific tracked sensor units can be mounted on a stationary location, such as a wall or a stationary stand. In this case, the PSD tracking device 100 tracks the stationary tracked sensor units in addition to the tracked sensor unit(s) 110 attached to the object(s) 120 to be tracked and uses the stationary tracked sensor units to compute a frame of reference that is common to both the moveable PSD tracking device 100 and the other moveable tracked sensor units 110.

In a possible embodiment, since the PSD tracking device 100 requires line-of-sight in order to detect the light spots from the tracked sensor unit 102 with its PSDs 102, multiple PSD tracking devices positioned in different locations can be employed to ensure that at least PSD tracking device is able to have a view of the tracked sensor unit 110 that is not occluded. In order for PSD tracking devices to be synchronized in a common coordinate system, all the PSD tracking devices can either be calibrated beforehand at known positions and remain stationary is such known positions, or alternatively, the PSD tracking devices could all use a set of stationary light spots as a frame of reference, for example by placing one or more tracked sensor units on one or more walls so that at least one of the stationary tracked sensor units is visible to each of the PSD tracking devices.

In various embodiments of the present invention, multiple tracked sensor units can be clustered together in various fashions. For example, in an embodiment in which a rigid object is to be tracked and a single light spot source is insufficient to provide line-of-sight, multiple light spot sources can be placed around the object to improve the likelihood that one of the light spot sources will have line-of-sight with the PSD tracking device 100 (or at least one of multiple PSD tracking devices). In this case, given that the object is rigid, only one IMU is needed to measure the orientation of the object. Therefore, a single tracked sensor unit 110 can be customized to have more than one light spot source 112. For example, the tracked sensor unit 110 can have multiple LEDs arranged on different sides/faces if the object 120 to be tracked. Examples of such rigid objects to be tracked can include transducers (e.g., ultrasound), surgical instruments, virtual reality (VR) and augmented reality (AR) headsets, and/or gaming accessories such as controllers, paddles, fake guns, etc. In an embodiment in which a non-rigid object is to be tracked, multiple tracked sensor units can be arranged into a mesh, for example for tracking gloves, body suits, clothes, etc. An advantage of treating multiple tracked sensor units as being part of one mesh is that in some cases supplying power and transmitting IMU data can be shared and consolidated between the mesh of tracked sensor units.

Figure 2:
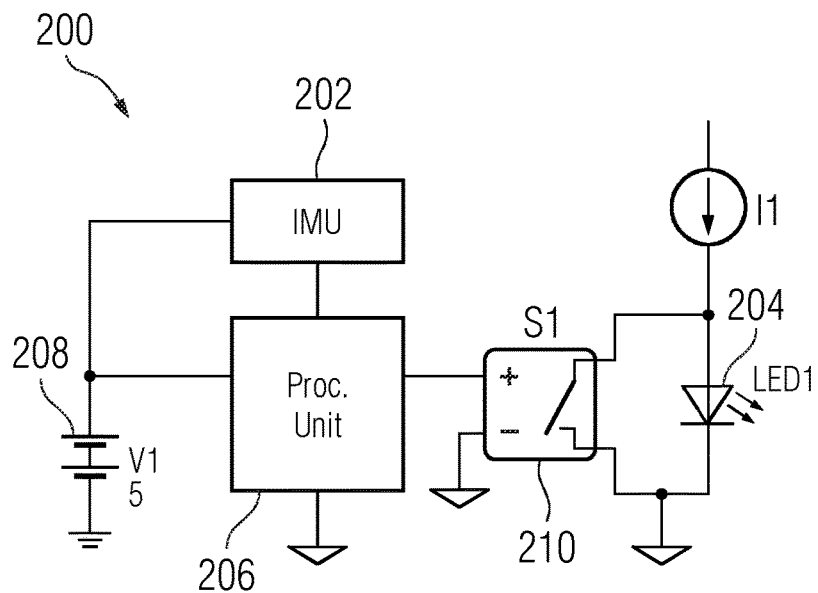
FIG. 2 illustrates a block diagram of a tracked sensor unit according to an embodiment of the present invention.

FIG. 2 illustrates a block diagram of a tracked sensor unit 200 according to an embodiment of the present invention. The tracked sensor unit 200 of FIG. 2 is attached to an object to be tracked (not shown in FIG. 2). The tracked sensor unit 200 of FIG. 2 can be used to implement tracked sensor unit 110 of FIG. 1 in an embodiment of the present invention. As shown in FIG. 2, the tracked sensor unit 200 includes an inertial measurement unit (IMU) 202, a light emitting diode (LED) 204, a processing unit 206, a power source 208, and a voltage controlled switch 210.

The IMU 202 can be implemented using a 9 axis IMU with electronics for bias. The IMU 202 can include one or more gyroscopes to measure rotational rate measurements with respect to three axes, one or more accelerometers to measure linear acceleration with respect to three axes, and one or more magnetometers to measure a magnetic heading with respect to three axes. The output of the IMU 202 at a given time point can include 9 raw readings (i.e., 3 rotation measurements, 3 acceleration measurements, and 3 magnetic heading measurements). Examples of 9 degree of freedom IMUs that can be used include Bosch BNO-055 and Invense MPU9250, but the present invention is not limited thereto.

The LED 204 can be implemented using a high efficiency laser based LED with a bias circuit. The power source 208 provides power to IMU 202, processing unit 206, and LED 204. The power source 208 can be a high energy (e.g., lithium ion) battery pack. In an advantageous embodiment, the processing unit 206 of the tracked sensor device 200 can be a microcontroller/microprocessor, but the present invention is not limited thereto and any other type of embedded processor or multiple processors can be used as well. In an advantageous embodiment, the processing unit 206 has wireless connectivity and can send and receive messages/data using a wireless communication protocol. For example, the processing unit 206 can establish a Bluetooth connection with the PSD tracking device and send and receive messages via Bluetooth. The processing unit 206 has an interface with the IMU 202 and receives the measurements output from the IMU 202. In an advantageous embodiment, the IMU 202 may only provide rotational measurements to the processing unit 206, but it is also possible that the processing unit 206 receives all of the 9 raw sensor readings measured by the IMU 202. The processing unit 206 may perform one or more algorithms (e.g., Kalman filtering) to filter and stabilize the raw sensor readings from the IMU 202. The processing unit 206 transmits a stream of 3 degree of freedom orientations corresponding to the rotational measurements from the IMU 202 via the wireless communication protocol (e.g., Bluetooth). For example, the processing unit 206 through its wireless connection can stream out the IMU orientation (rotation) measurements at a certain frequency. The processing unit 206, through its wireless connection, also receives messages (e.g., from a processing unit of the PSD tracking device) regarding pulse and duty cycle of LED strobing. The processing unit 206 controls strobing of the LED 204 via the switch 210. The switch 210 allows bypassing the current through the LED 204 to turn the LED 204 off and on. Thus, the processing unit 206 uses the switch 210 to turn the LED 204 on and off to control the LED strobing.

Figure 3:
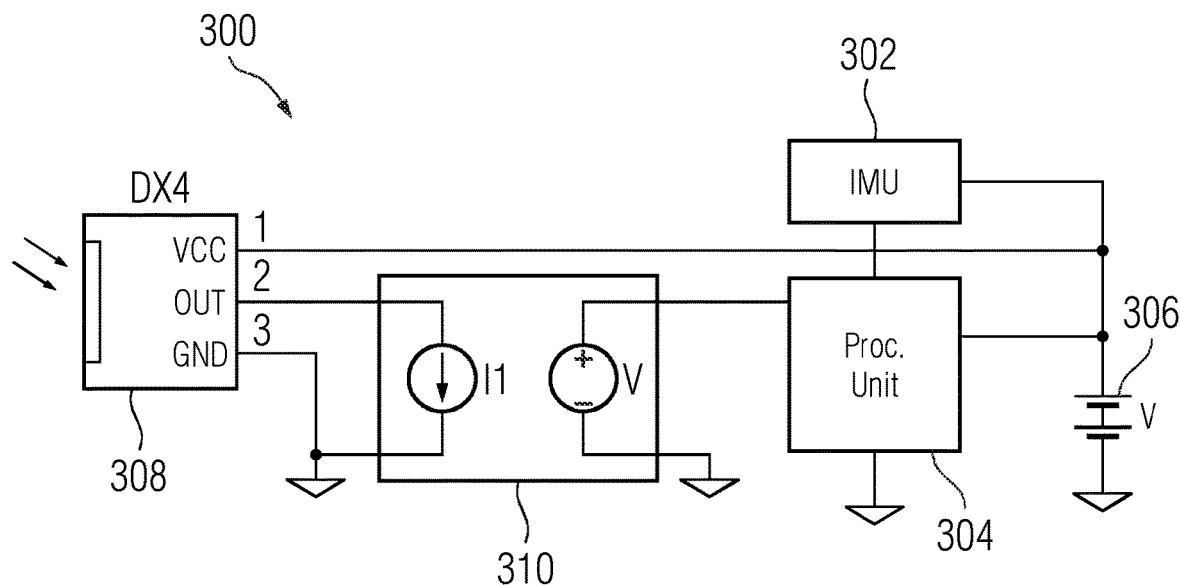
FIG. 3 illustrates a block diagram of a position sensitive detector (PSD) tracking device according to an embodiment of the present invention.
Figure 4:
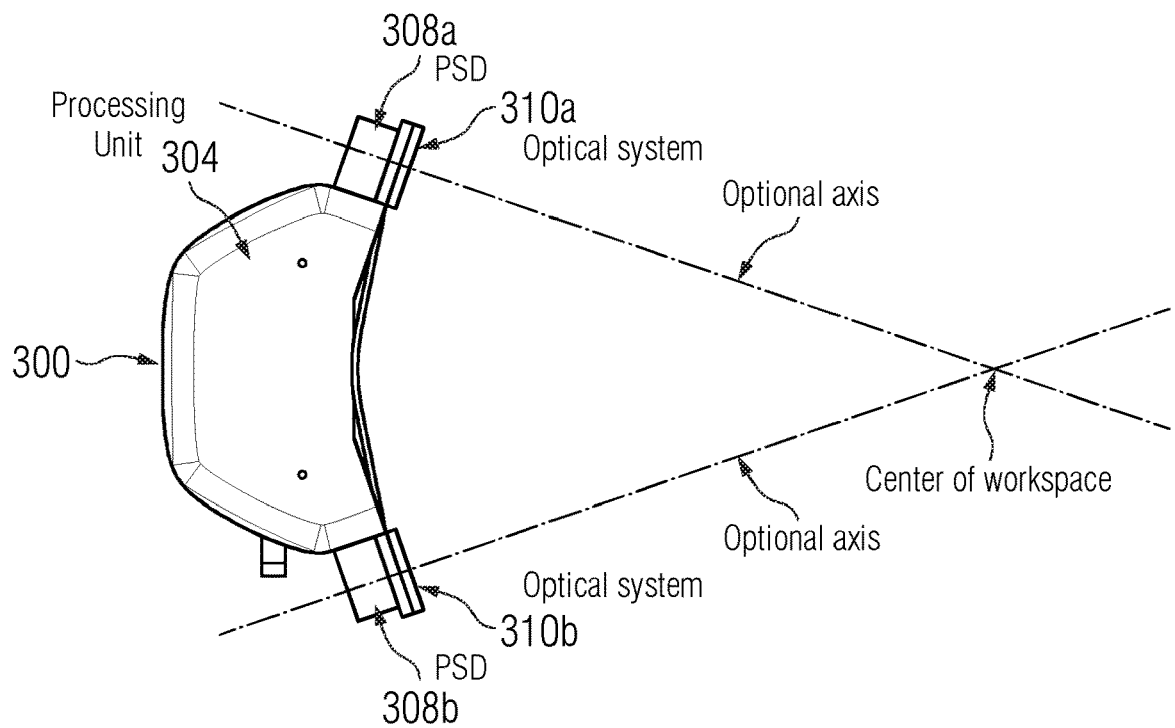
FIG. 4 shows an overhead view of the PSD tracking device; according to an embodiment of the present invention
Figure 5:
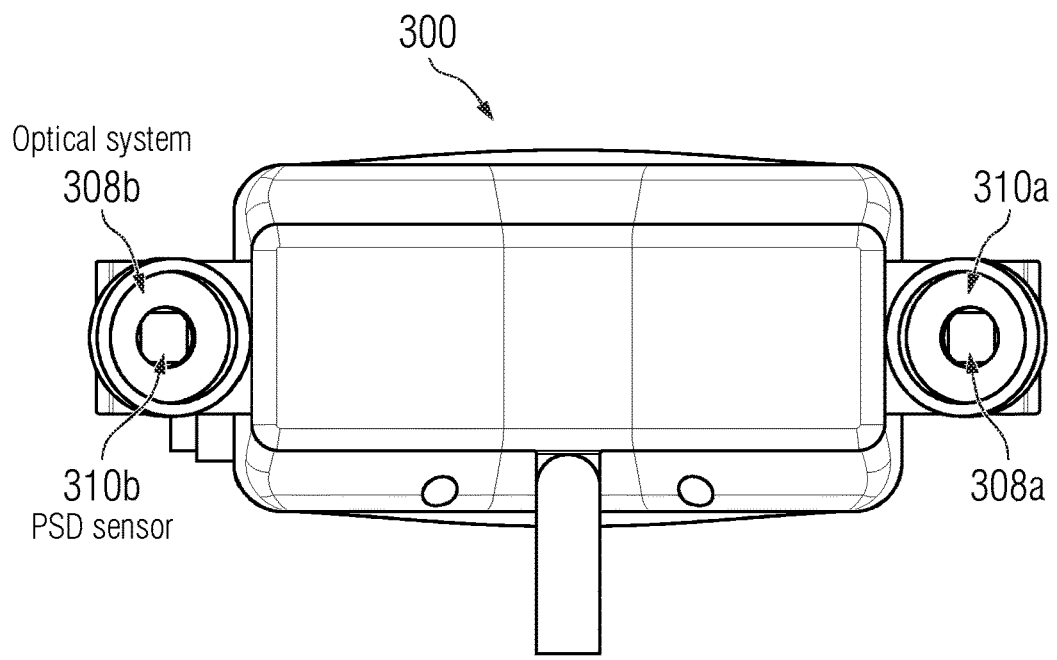
FIG. 5 shows a front view of the PSD tracking device according to an embodiment of the present invention.

FIG. 3 illustrates a block diagram of a PSD tracking device 300 according to an embodiment of the present invention. The PSD tracking device 300 of FIG. 3 can be used to implement PSD tracking device 100 of FIG. 1 in an embodiment of the present invention. As shown in FIG. 3, the PSD tracking device 300 includes an inertial measurement unit (IMU) 302, processing unit 304, a power source 306, and a pair of position sensitive detectors (PSDs) 308 arranged to form a stereo pair with a certain base-line and vengeance angle. It should be noted that although the PSD tracking device includes a pair of PSDs, the block diagram of FIG. 3 only shows a single PSD 308 for ease of explanation and the description of PSD 308 applies to both PSDs in the PSD tracking device. An exemplary arrangement of the pair of PSDs is shown in FIGS. 4 and 5. The PSD tracking device 300 also includes a set of optics (shown in FIGS. 4 and 5) to focus the light spots in the tracking environment onto each PSD 308. The IMU 302 provides local rotational measurements for the PSD tracking device 300. The IMU 302 can also provide linear acceleration and magnetic heading measurements for the PSD tracking device 300. The IMU 302 of the PSD tracking device 300 can be implemented using a 9 axis IMU with electronics for bias, similar to the IMU 202 of the tracked sensor unit 200 described above. The power source 306 provides power to processing unit 304, IMU 302, and each PSD 308. The power source 306 can be a high energy (e.g., lithium ion) battery pack.

The term "position sensitive detector" (PSD) refers to an optoelectronic sensor that utilizes photodiode surface resistance to measure the position of the integral focus of an incoming light signal by converting a light spot on the PSD sensor surface into a continuous electrical signal corresponding to the focal position of the light spot. PSDs are typically utilized as feedback elements for optical alignment systems such as lasers, mirror control, microscope focusing, and fiber systems such that a laser beam/collimated optical beam hits a center of the PSD surface and zero current is output. While they are simple and inexpensive to manufacture, the linearity decreases as the spot moves away from the center. According to an advantageous aspect of the present invention, the PSD tracking device 300 utilizes two PSDs 308 together with optical lenses to create a tracking device that is used for tracking a position of an object in 3D space. In an advantageous embodiment, each PSD 308 generates a current that is proportional to the location of the incident light spot in 2D. In an exemplary implementation, 2D tetra-lateral PSDs are used to provide continuous position measurement of the incident light spot in 2D. In this case, each PSD 308 includes a single square silicon PIN diode with a resistive layer. When there is an incident light on the active area of the PSD sensor, photocurrents are generated and collected from four electrodes placed at the four corners of the PSD 308. For each PSD 308, the location of the light spot in 2D is given by a function of the four currents collected from the four corners of the PSD 308:

$$[x,y]=f(\beta,b;I_1,I_2,I_3,I_4). \quad (1)$$

Here, f is a nonlinear transfer function with parameters $\beta$ and functional b that maps the four currents to accurate 2D locations of the light spot. Thus, two PSDs each return respective two sets of 2D coordinates corresponding to respective 2D locations of the focal point of the light spot with respect to each PSD, and these 2D coordinates are redundant with respect to the 3D location of the focal point of the light spot in space. Stereo triangulation can then used to obtain this 3D point from the two sets of 2D coordinates. Since the light originated from the tracked sensor unit (e.g., tracked sensor unit 200 of FIG. 2) attached to an object to be tracked, this 3D location provides a position in 3D space of the tracked sensor unit and thus the object to be tracked.

The processing unit 304 of the PSD tracking device 300 includes a digitizer that converts the analog current output from the PSDs, applies the transfer function as in equation (1) and performs stereo triangulation.

As described above, in an advantageous embodiment, two PSDs arranged in a stereo arrangement are used to provide two sets of 2D coordinates for a location of a light spot, and these coordinates are redundant with respect to the 3D location of the light spot. In an alternative embodiment, the number of values can be reduced to just three arising out of three 1D PSDs arranged in a specific configuration to enable point triangulation in space.

The processing unit 304 of the PSD tracking device 300 can be implemented using any type of embedded processor, such as a graphics processing unit (GPU), advanced RISC (ARM) processor, microprocessor/microcontroller, central processing unit (CPU), or any combination thereof. The processing unit 304 may be implemented as a multiple processing unit that utilizes multiple processors. The processing unit 304 of the PSD tracking device 300 has the functionality to interface to the IMU 302. Furthermore, processing unit 304 has wireless connectivity and communicates with the tracked sensor units (e.g., tracked sensor unit 200 of FIG. 2) to adjust the frequency and duty cycle of each LED within the tracked sensor unit and also synchronize the PSD reading with the measurements from the tracked sensor unit through a handshake protocol. The processing unit 304 can send messages/commands to the processing unit of the tracked sensor unit to control the frequency and duty cycle of each LED via a wireless communication protocol. As shown in FIG. 3, the currents generated by each PSD 308 can be converted to voltages, which are input to the processing unit 304. As each PSD 308 generates a continuous electrical signal, the corresponding voltages may be converted to a digital signal using an analog-to-digital converter before being fed to the processing unit 304. Alternatively, the processing unit 304 may include a digitizer and that performs this analog-to-digital conversion. The processing unit 304 can compute a respective set of 2D coordinates from the signal received from each PSD 308 and then perform stereo triangulation to calculate the 3D location of the tracked sensor unit/object. The processing unit 304 can estimate the overall synchronized 6D pose of each tracked sensor unit/object being tracked using the orientation measurements from the tracked sensor unit's IMU and the position calculated through stereo triangulation based on the position measurements of the PSDs 308. The processing unit 304 also has the functionality to communicate the overall synchronized 6D pose of each tracked sensor unit being tracked to an end user device, such as a computer station or a mobile device. For example, the processing unit 304 can communicate the 6D pose information to a computer station or mobile device via a universal serial bus (USB)-universal asynchronous receiver-transmitter (UART) interface.

FIGS. 4 and 5 illustrate a possible design of the PSD tracking device 300 according to an embodiment of the present invention. FIG. 4 shows an overhead view of the PSD tracking device 300. FIG. 5 shows a front view of the PSD tracking device 300. As shown in FIGS. 4 and 5, the PSD tracking device 300 includes two PSDs 308a and 308b (also referred to a PSD sensors) arranged to form a stereo pair and a respective optical system 310a and 310b arranged in front of each PSD 308a and 308b. The optical system 310a and 310b for each PSD 308a and 308b includes one or more lens to light spots in a workspace object tracking onto the surface of the PSD 308a and 308b. In an exemplary embodiment, each optical system 310a and 310b can be implemented using a biconvex lens disposed in front of the respective PSD 308a and 308b to focus light in the workspace onto the respective PSD 308a and 308b. Alternatively, the same effect of focusing of a point source of light can be achieved by other optical setups, such as a cylindrical lens or spherical surfaces. As shown in FIG. 4, the optical axes of the two optical systems 310a and 310b meet at a center of the workspace. It is to be understood that the components shown in the block diagram of FIG. 3 are included within the PSD tracking device 300 shown in FIGS. 4 and 5.

Figure 6:
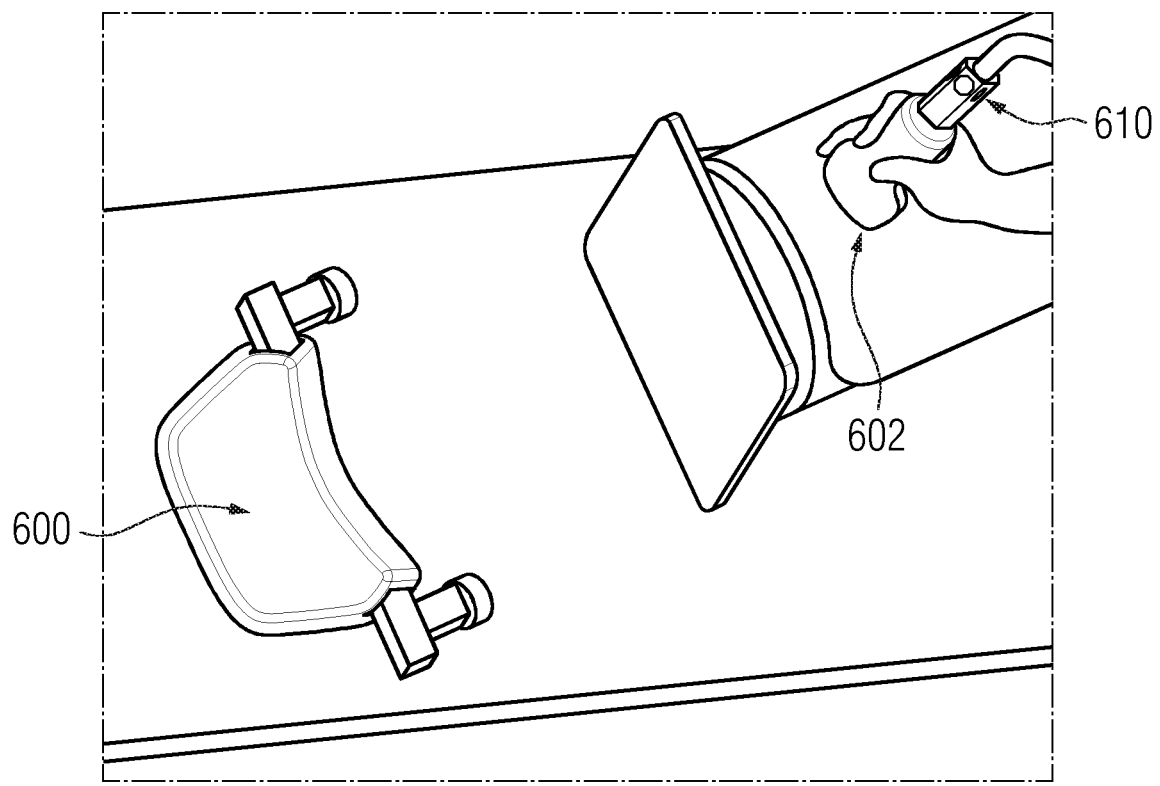
FIG. 6 illustrates tracking an ultrasound probe with the PSD based tracking system according to an exemplary embodiment of the present invention.

FIG. 6 illustrates tracking an ultrasound probe with the PSD based tracking system according to an exemplary embodiment of the present invention. As shown in FIG. 6, an ultrasound probe 602 is tracked using a PSD tracking device 600 and a tracked sensor unit 610 attached to the ultrasound probe 602. The PSD tracking device 600 is implemented similar to the PSD tracking device 300 shown in FIGS. 3, 4, and 5. The tracked sensor unit 610 is implemented similar to the tracked sensor unit 200 shown in FIG. 2, but with multiple LEDs arranged around the ultrasound probe.

According to an embodiment of the present invention, various algorithmic techniques are used to calibrate the PSDs, perform the triangulation to determine the 3D position of tracked sensor unit, synchronize the LED strobing with the PSD read-out and following triangulation results, and synchronize the IMU read outs (from the tracked sensor unit) with the triangulation results. These operations are described as follows for an advantageous embodiment.

PSD Calibration

Each PSD gives the 2D image point of the LED point source. Thus, like a stereo setup, the PSD calibration can be resolved into an intrinsic calibration and an extrinsic calibration. The intrinsic calibration includes the focal length, the principal point, skew angle, and distortion parameters. The focal length, skew angle, and principal point have direct parallels with computer vision cameras. However, the distortion for PSD is different from CMOS/CCD type sensors typically used in computer vision. The biconvex lenses uses to focus the light produce barrel distortions, whereas the PSD sensor itself produces a pincushion distortion. Ideally, if the electrical center of the PSD and the optical center of the lens coincide, the two distortions can almost cancel out. However, this may not be achieved in practice. Thus, according to an advantageous embodiment, two-dimensional Berstein basis polynomials of degree n can be used, which are defined as:

$$(u',v') = \Sigma\Sigma \beta_{ij} b_{ij}(u,v). \quad (2)$$

To obtain projected points, a grid of LEDS, referred to as the "calibration target" that is fabricated to a certain tolerance is used to project N×M points in space. The grid can be moved around to cover the entire sensor area. Both the standard optical system parameters (i.e., focal length, skew angle, and principal point) and the distortion coefficient are obtained in an iterative algorithm of projecting known points, dewarping and recasting them in space. These calibrated parameters β and functionals b are stored and utilized to transform currents in 2D locations using equation (1). Once the individual PSD sensors have been calibrated, the calibration of extrinsic parameters of the stereo rig, given by the orientation and translation of the left PSD sensor (e.g., 308a in FIGS. 4 and 5) to the right PSD sensor (e.g., 308b in FIGS. 4 and 5) can be computed by iteratively solving for unknowns. These extrinsic parameters are also used in the triangulation of the 3D location, as described in greater detail below.

Another quantity to be calibrated for the PSD tracking device is the relative position between the IMU sensor of the PSD tracking device and the left PSD sensor, which can be used as a reference coordinate for all measurements without loss of generality. This can be achieved by incorporating and IMU in the grid of LEDs, which is also fabricated to a certain desired tolerance. Estimating orientation of the LED calibration body using the optical system and comparing it with the orientation computed using the IMU in the grid of LEDs gives the relative orientation between the PSD sensor and the IMU sensor of the PSD tracking device. It is to be understood that although the embodiments described herein use the left PSD to establish the reference coordinate system for all measurements, the present invention is not limited thereto and either PSD may be used as the reference PSD. This calibrated parameter value is used in the computation of the output 6 DoF pose as described below by equation (3).

The calibration process of estimating the required parameters by using the calibration target can be completed prior to the usage of the device (e.g., during manufacturing and assembly) and stored in a memory or storage of the tracking device or another computer device to which the tracking device is connected. During the time of operation, these parameters can be retrieved and used for the respective computations.

PSD Triangulation

To compute the 3D position of the LED source, stereo geometry is used to construct a 3D point from two 2D projections. However, according to an advantageous embodiment of the present invention, to obtain true geometric projections given the distortion of the PSD sensors, the inverse of dewarping as computed in equation (2) is first applied to each measured 2D point.

Figure 7:
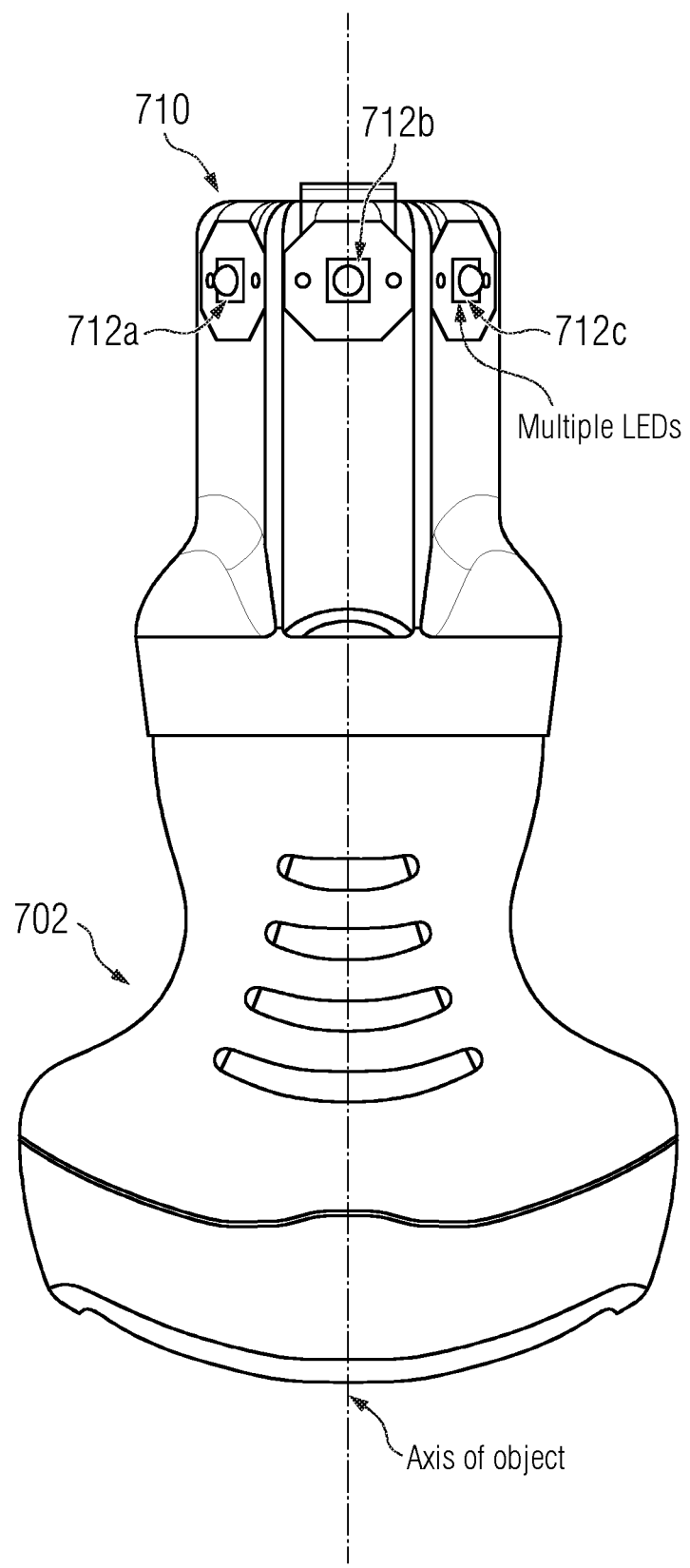
FIG. 7 illustrates the use of multiple light emitting diodes (LEDs) in a tracked sensor unit according to an embodiment of the present invention.

FIG. 7 illustrates the use of multiple LEDs in a tracked sensor unit according to an embodiment of the present invention. As shown in FIG. 7, the sensing unit 710 attached to an object 702 to be tracked includes multiple LEDs 712a, 712b, and 712c, arranged around the axis of the object 702. In a case in which the tracked sensor unit comprises multiple LEDs, such as the example shown in FIG. 7, the position of the LEDs with respect to each other and with respect to the object coordinate system must be determined. If multiple LEDs are visible to the PSDs simultaneously, then this process is simple as each LED+IMU combination can return a pose, and the unknown values of the relative positions of the LEDs with respect to the object coordinate system can be estimated by simple inversion. In a case in which only one LED is visible, then a calibration akin to a pivot calibration, wherein the object is rotated/swung around each of its axes, is performed. The center of this rotation gives the unknown quantity of the relative position of the LED with respect to the object coordinate system.

LED Strobing and Duty Cycle Assignment

Figure 8:
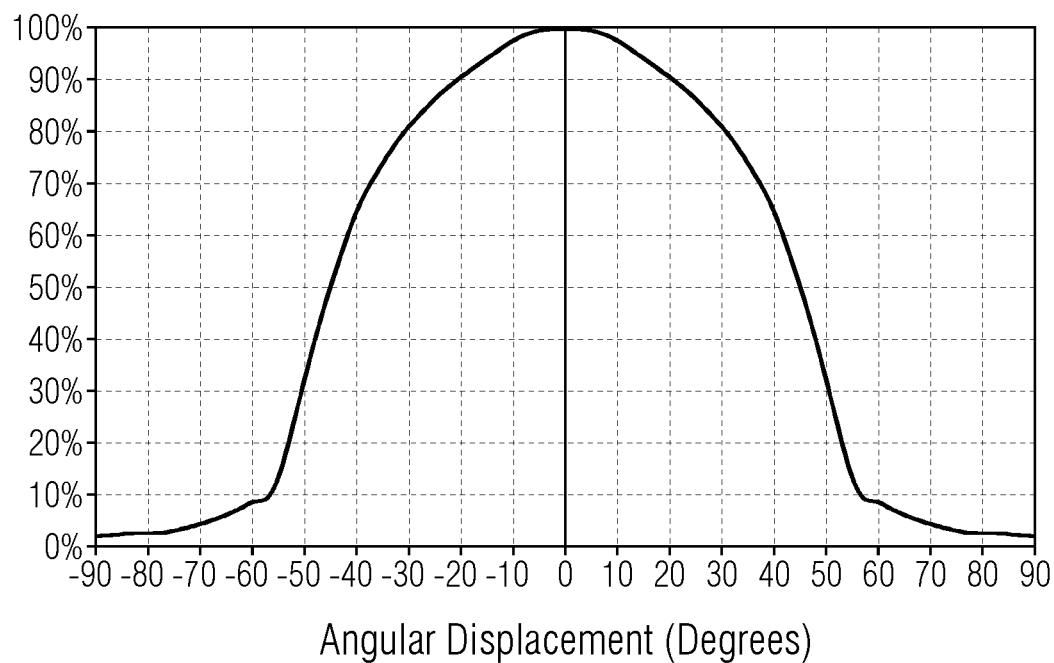
FIG. 8 illustrates an exemplary radiation pattern of a high efficiency laser based LED.

The frequency of the current induced in each PSD is a function of the frequency of the LED current. Thus, different protocols for signal multiplexing can be employed. These could be either some form of time division multiplexing or frequency multiplexing, or any such combination. This enables several tracked sensor units to be tracked simultaneously. FIG. 8 illustrates an exemplary radiation pattern of a high efficiency laser based LED. Even with large viewing angles, it may not be possible to rotate the tracked sensor unit a full 360 degrees without losing sight of the LED. Thus, for some practical applications, the tracked sensor unit may have an arrangement of four or more LEDs arranged around the axis of the object to be tracked. In order to optimize the power consumption, only the LEDs that are visible to the PSDs may be turned on or take part in the communication protocol. The relative orientation of the tracked object with respect to the PSD tracking device (based on the IMU measurements of the tracked sensor unit) may be used by the processing unit of the tracked sensor unit to determine which LEDs are currently visible. A past history may also be used to track potential visible LEDs.

It is to be noted that the LED light can also be employed as means to communicate digital data to the PSD tracking device, for example by modulating the intensity of the LED light. Optical wireless communication can be a replacement for radio frequency communication such as Bluetooth or WiFi, and can be an alternative method for transmitting the IMU orientation information to the PSD tracking device.

Estimation of 6 Degree of Freedom (DoF) Pose From Inertial and PSD Measurements

The 3D position of the LED source with respect to the left PSD sensor (determined by triangulation) is given by p. The 3D orientation of the IMU attached to the LED source (i.e., the tracked sensor unit) is given by $^g R_{IMU_0}$. If the fixed relative orientation between the object body and the attached IMU is given by $^{IMU_0} R_0$, then $^g R_0 = {}^g R_{IMU_0} \times {}^{IMU_0} R_0$ is the 3D orientation of the object body with respect to gravity and magnetic north. Likewise, the relative orientation of the IMU attached to the PSD tracking device is given by $^g R_{IMU_p}$ and the fixed relative orientation between the left PSD sensor and the attached IMU is given by $^{IMU_p} R_p$. Thus, the 3D orientation of the left PSD sensor with respect to gravity and magnetic north is given by $^g R_p = {}^g R_{IMU_p} \times {}^{IMU_p} R_p$. The 3D orientation of the tracked sensor unit with respect to the left PSD sensor, can then be calculated as:

$$^p R_0 = {}^g R_p^{-1} \times {}^g R_0. \quad (3)$$

The pair $\langle p | {}^p R_0 \rangle$ provides the raw 6 DoF pose of the tracked sensor unit with respect to the left PSD sensor of the PSD tracking device. Further filtering techniques, such as Kalman estimators, particle filters, etc., can be applied (e.g., by the processing unit of the PSD tracking device) to post-process these raw values and provide a filtered response. The filtering is straight forward in the case of a single LED source, as no additional information is available.

In the case of a multi-LED system, the position of the LED needs to be transformed to the origin of the object coordinate system. In an embodiment in which the LEDs are arranged around an axis of the object to be tracked such the object may be continuously visible as the object is rotated object its axis, the location of the origin of the object coordinate system can be computed from the position of the ith LED as follows: $p_i + {}^p R_0 \times q_i$. Here, $p_i$ is the measured position of the LED in the left PSD sensor coordinates and $q_i$ is the position of the LED with respect to the object coordinate system. This position $q_i$ can be estimated as part of the calibration process or known from fabrication up to a certain tolerance value.

Figure 9:
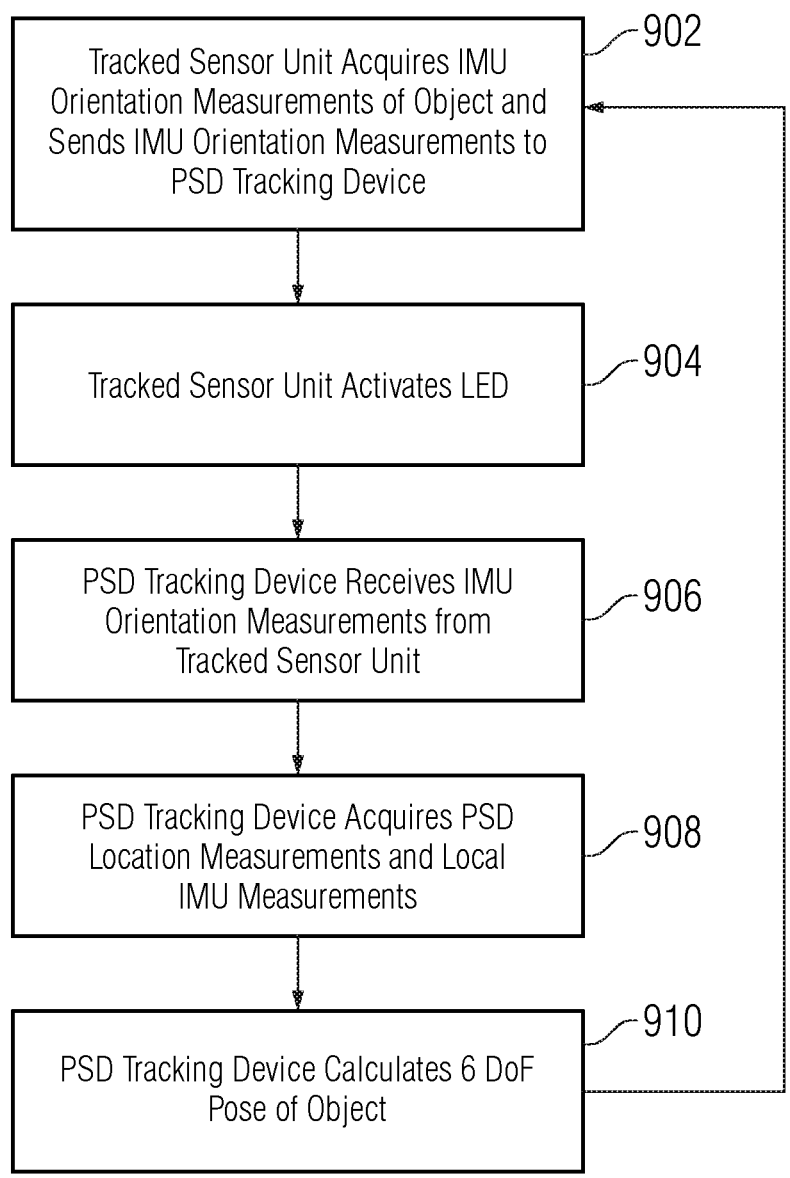
FIG. 9 illustrates a method of tracking a 6D pose of an object using a PSD based tracking system according to an embodiment of the present invention.

FIG. 9 illustrates a method of tracking a 6D pose of an object using a PSD based tracking system according to an embodiment of the present invention. At step 902, the tracked sensor unit, which is attached to the object being tracked, acquires IMU orientation measurements of the object using the IMU of the tracked sensor unit and sends the IMU orientation measurements to the PSD tracking device. For example, the microcontroller of the tracked sensor unit can transmit to the IMU orientations measurements to the PSD tracking device via a wireless communication protocol, such as Bluetooth or WiFi. At step 904, the tracked sensor unit activates the LED. When the tracked sensor unit transmits the IMU orientation measurements to the PSD tracking device, the microcontroller of the tracked sensor unit also controls at least one LED to turn on to provide a light spot source from which the PSDs of the PSD tracking device can detect the location of the tracked sensor unit. In an embodiment in which the tracked sensor unit includes multiple LEDs, the microcontroller of the sensing unit can determine, based on the IMU orientation measurements, which of the LEDs are facing the PSD tracking device and activate only those LEDs that are currently facing the PSD tracking device.

At step 906, the PSD tracking device receives the IMU orientation measurements from the tracked sensor unit attached to the object being tracked. Since the tracked sensor unit activates the LED when it sends the IMU orientation information, the receipt of the IMU orientation information from the tracked sensor unit by the PSD tracking device can act as a message that alerts the PSD tracking device of when the LED will be turned on. At step 908, the PSD tracking device acquires PSD location measurements from each of the PSD in the pair of PSDs and acquires local IMU measurements from the IMU attached to the PSD tracking device. Each PSD generates currents based on the position of the light spot generated by the LED focused on the surface of the PSD by the optical system, and the currents generated by each PSD define a 2D location of the LED with respect to that PSD. At step 910, the PSD tracking device calculates the 6 DoF pose of the object. The 6 DoF pose of the object includes the 3D position and 3D orientation of the object. The 6 DoF pose can be calculated with respect to a coordinate system of the PSD tracking device. The 3D position of the object is calculated by stereo triangulation based on the 2D locations of the LED measured by each PSD of the pair of PSDs, as described above. The 3D orientation of the object in the coordinate system of the PSD tracking device (e.g., with respect to the left PSD) is calculated by computing the 3D orientation of the tracked sensor unit (which is attached to the object) with respect to the reference (e.g., left) PSD based on the IMU orientation measurements received from the tracked sensor unit and the local IMU measurements of the PSD tracking device, as described above.

The method then returns to step 902 and steps 902-910 are repeated to provide a stream of IMU measurements from the tracked sensor unit to the PSD tracking device and compute a stream of 3D positions and 3D orientations of the object in order to track the object in real-time. The stream of 6D poses (3D positions and 3D orientations) of the object can be output to an external computer device or mobile device in real time as the 6D poses are computed. The tracked pose of the object can be displayed on the computer device or mobile device and/or used as input to further algorithms, for example for medical image processing or interventional navigation (in an embodiment in which an ultrasound probe or surgical tool is the object being tracked).

Figure 10:
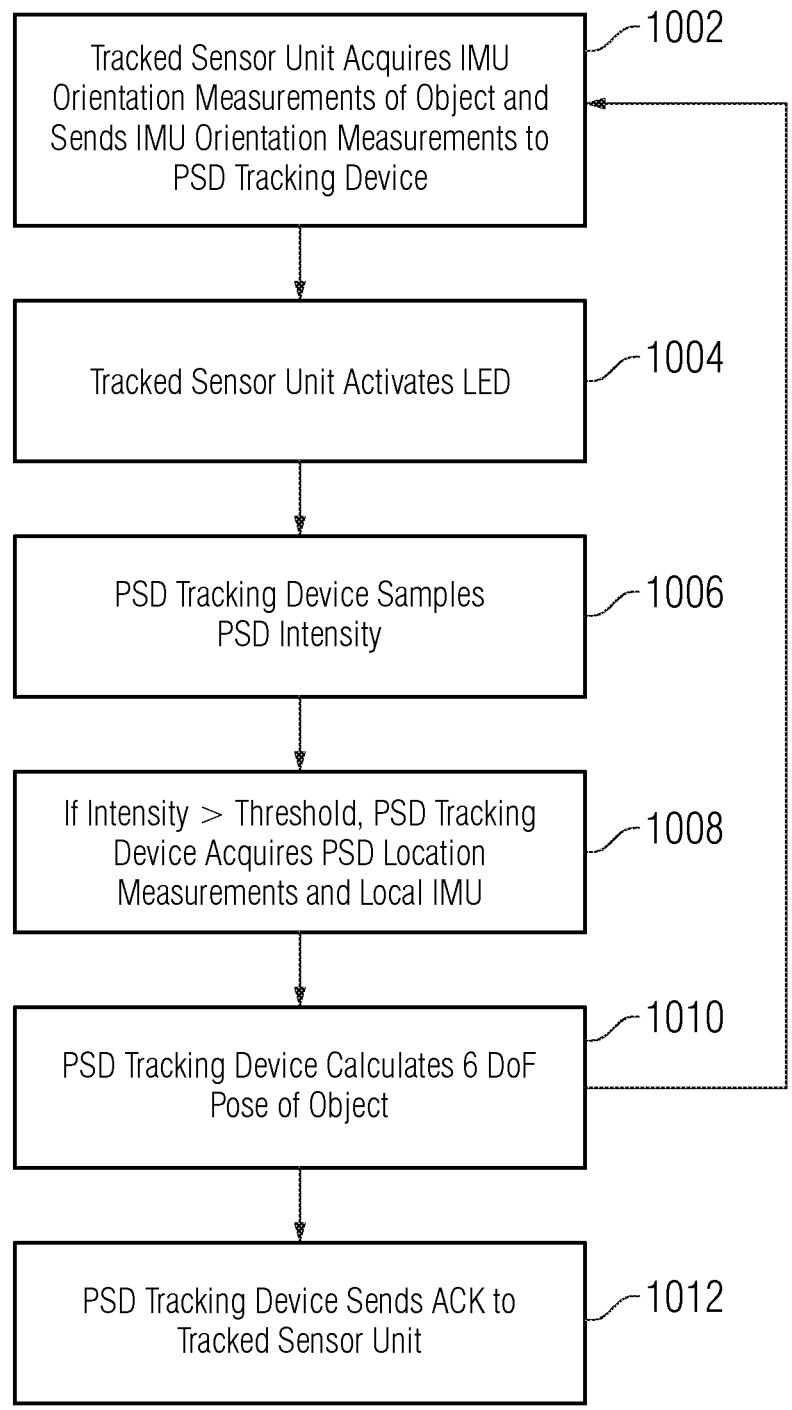
FIG. 10 illustrates a tracking a 6D pose of an object using a PSD based tracking system with a handshake protocol between the PSD tracking device and the tracked sensor unit according to an embodiment of the present invention.

In a possible embodiment of the present invention, the PSD tracking device and tracked sensor unit can synchronize the PSD reading and the activation of the LED(s) through a handshake protocol. FIG. 10 illustrates a tracking a 6D pose of an object using a PSD based tracking system with a handshake protocol between the PSD tracking device and the tracked sensor unit according to an embodiment of the present invention. At step 1002, the tracked sensor unit, which is attached to the object being tracked, acquires IMU orientation measurements of the object using the IMU of the tracked sensor unit and sends the IMU orientation measurements to the PSD tracking device. At step 1004, the tracked sensor unit activates one or more LED. At step 1006, the PSD tracking device samples the PSD intensity of the light spot generated by the LED by using the digitizer to obtain the sum of the currents produced by the PSDs. At step 1008, if the intensity of the light is greater than a threshold, indicating to the PSD tracking device that the LED was indeed turned on, the PSD tracking device acquires the PSD locations measurements from each PSD and the local IMU measurements. A respective 2D location is acquired from each PSD by applying the transformation of equation (1) to the measured currents. At step 1010, the PSD tracking device calculates the 6 DoF pose of the object based on the location measurements from the PSDs, the IMU orientation measurements received from the tracked sensor unit, and the local IMU measurements of the PSD tracking device. At step 1012, the PSD tracking device sends an acknowledgement (ACK) to the tracked sensor unit. The ACK message is provided to indicate to the tracked sensor unit that the tracking device received its message, and that it can proceed to deactivate the LED and start the next cycle. As part of the double handshake, the tracked sensor unit will acknowledge the ACK in the next LED activation cycle at the time sending IMU measurements (e.g., by incrementing the packet number or modulo-N LED number). Similar to the method of FIG. 9, the method of FIG. 10 is also repeated to compute a stream of 6 DoF poses in order to track the object in real-time.

Figure 11:
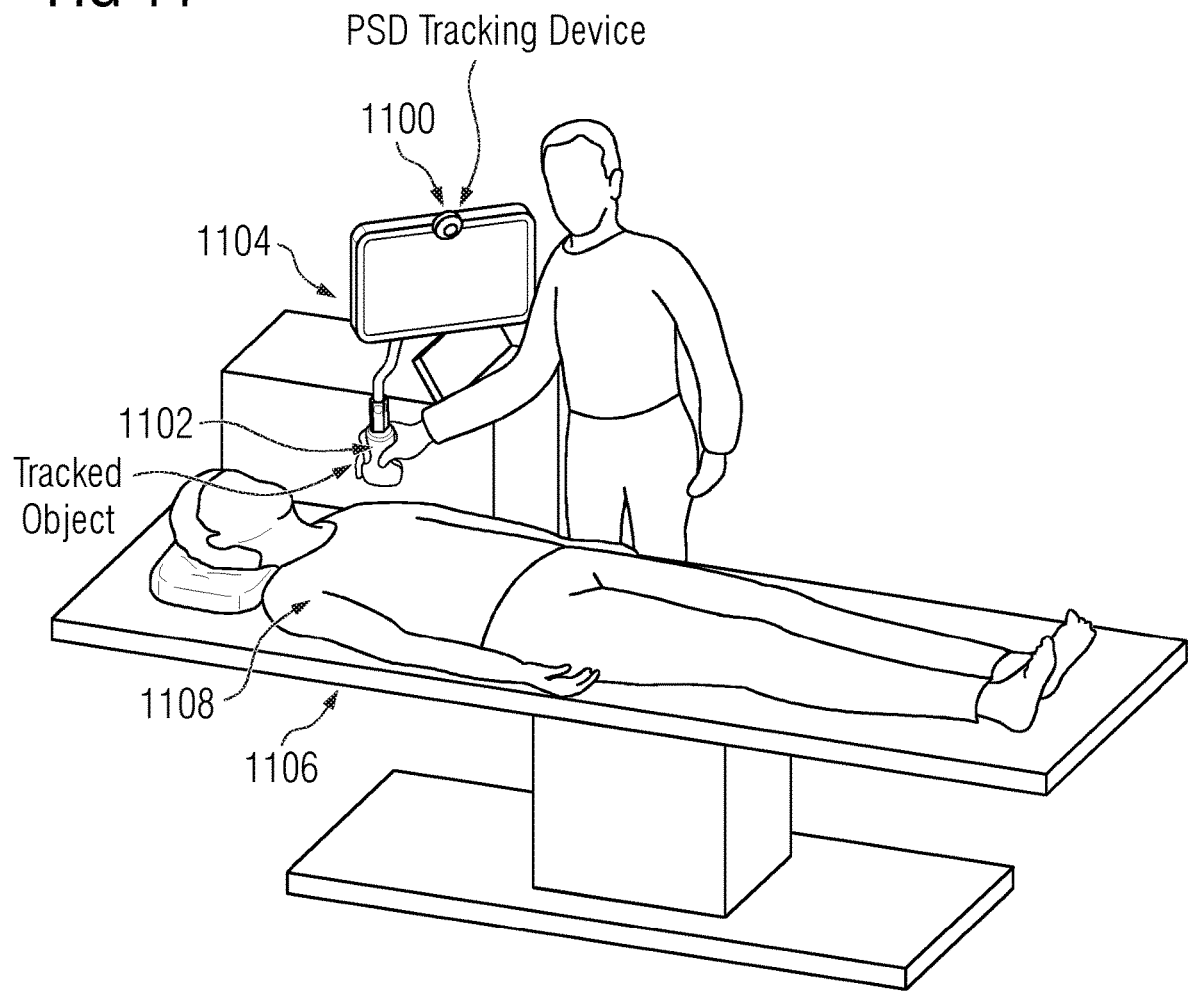
FIG. 11 illustrates the use of the PSD based tracking system to in a medical application to track an ultrasound transducer according to an embodiment of the present invention.

FIG. 11 illustrates the use of the PSD based tracking system to in a medical application to track an ultrasound transducer according to an embodiment of the present invention. As shown in FIG. 11, in this possible embodiment, the PSD tracking device 1100 is mounted on top of an Ultrasound scanner 1104. A tracked sensor unit is mounted on top of the casing of a handheld ultrasound transducer 1102, so that the ultrasound transducer 1102 can be tracked by the PSD tracking device 1100. In a possible implementation, an additional tracked sensor unit can also be mounted on the patient's table 1106, to establish a stationary frame of reference for the coordinate system of the PSD tracking device 1100 and the transducer's position. One or more additional tracked sensor units can also be placed on the patient 1108 at known anatomical locations, so that they can be used as landmarks to understand where the transducer 1102 is with respect to the patient's anatomy. Such information can then be used to aid the workflow of the ultrasound examination. For example, based on such information, the PSD based tracking system could determine whether the transducer 1102 is on the left side or right side of the patient 1108, and therefore help differentiate between images of symmetric organs (e.g., left kidney vs. right kidney). In addition the PSD based tracking system could provide additional information to algorithms for the automatic detection of organs in the ultrasound images, thereby reducing the search space. For example, if it is known that the transducer 1102 is positioned on the patient's neck, all abdominal organs can be automatically ruled out and the detection algorithm can focus on discerning only neck structures, such as the thyroid, carotid artery, etc.

Figure 12:
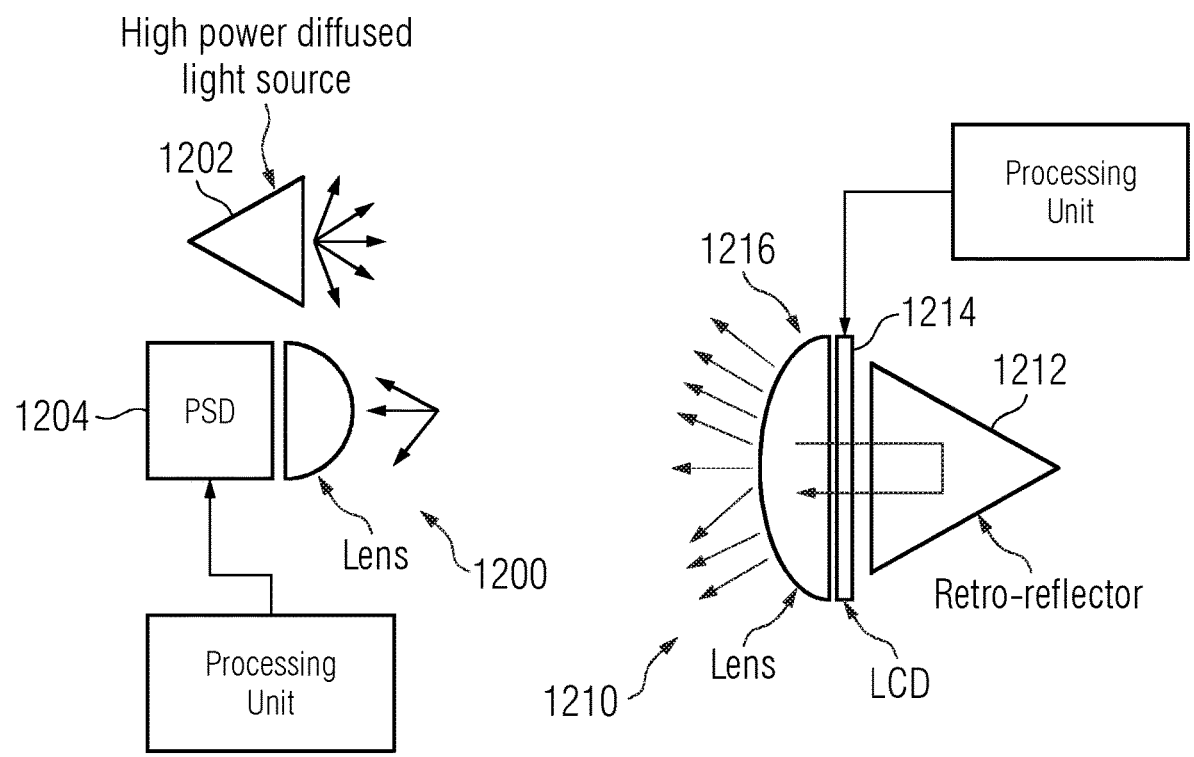
FIG. 12 illustrates a PSD based pose tracking system with a low power tracked sensor unit according to an embodiment of the present invention.

In the embodiments describe above, an LED or a similar light source is attached to the object to be tracked along with sensors (IMU) and a processing unit, as shown in FIG. 2. With the availability of efficient LEDs, sufficient optical power can be delivered at relatively moderate to low currents and voltages. Nevertheless, power source size and weight (i.e., battery size) may limit the application of such tracked sensor units under certain conditions. For example, if the object to be tracked is a small handheld medical device, such as a needle, an ablator, or a pedicle screw, the goal would be to make the tracked sensor unit as small and light weight as possible. For such an application, an embodiment of the present invention is provided that provides a low power tracked sensor unit with an alternative means for obtaining the 3D position of the point source in the PSD. FIG. 12 illustrates a PSD based pose tracking system with a low power tracked sensor unit according to an embodiment of the present invention. As shown in FIG. 12, in this configuration, the PSD tracking device 1200 includes a high power light source 1202 attached to the PSD 1204. In the tracked sensor unit 1210, the LED light source is replaced by a combination of a retroreflector 1212, liquid crystal display (LCD) 1214, and lens assembly 1216. Such a system is different from conventional passive markers, which comprise of just a collection of retroreflective markers that are observed and then identified in a projection image. Since the PSD 1204 generates a signal for the average of all light spots, the modulation of the passive marker is necessary to distinguish its projection from that of others. This complete assembly typically takes a fraction of the power of most efficient LEDs. Alternatively, the lens 1216, LCD 1214, and retro-reflector 1212 combination shown in FIG. 12 can be replaced by a modulating retro-reflector (MRR) and lens combination. Typically MRRs are used in optical communications in which a laser source is used as an interrogator source. In an embodiment of the present invention, an un-collimated, diffused source of light is used to illuminate the retroreflector for all possible directions. The lens 1216 in front of the LCD 1214 or MRR is used to control the view angle. If the LCD 1214 or modulator is off, no light will be returned and thus no light spot will be formed on the PSDs 1204 of the PSD tracking device 1200. If the LCD 1214 or modulator is on, light will pass through the LCD 1214 or modulator and will be reflected back along the same path. This would give the retro-reflector 1212, LCD 1214, and lens 1216 combination an appearance of a "cat's eye" that can be opened or closed based on modulations of the LCD 1214 or modulator. Note that the optical power of the light source 1202 mounted on the PSD 1204 has to be at least four times that of the equivalent LED mounted on the tracked sensor unit to achieve comparable working distances. This assumes that there are not optical power losses in the LCD 1214, retroreflector 1212, or lens 1216.

Another alternative is to power the tracked sensor unit wirelessly using existing RFID technology. For example, battery-free ultra high frequency (UHF) RFID LED tags, such as Farsens Stella-LEDW703, are able to wirelessly receive power from UHF and can light up an LED. Additional power for the IMU and processing unit can be supplied with such technology as well.

Additional variations and extensions to the above described embodiments are provided as follows.

In a possible embodiment, the PSD tracking device can be equipped with a tracked sensor unit, and the entire tracking chain can be cascaded to increase the size of the workspace where the overall tracking system is operational.

In a possible embodiment, stationary tracked sensor units can be used to establish a coordinate system that can be used as a frame of reference by one or more PSD tracking devices, so that the PSD tracking devices can be moved and still be able to track other moveable tracked sensor units.

In a possible embodiment, multiple PSD tracking devices, which may not necessarily be pre-calibrated to each other, may be distributed around the workspace oriented in different directions. The tracked object itself can be used as a means to calibrate these distributed PSD tracking devices.

In a possible embodiment, miniaturized tracked sensor units can be attached to deformable bodies to track the position and orientation of select points on the instrumented deformable body. Various identification methods, such as flashing frequency and duty cycle of LED strobing, can be used as examples to resolve identification of each of the tracked sensor units by the PSD tracking device.

The embodiments described above use the earth's gravity and magnetic north to setup a global coordinate system. In an alternative embodiment, a permanent magnet may be attached to a fixe point (e.g., an ultrasound cart, or patient bed) with sufficient field strength. This permanent magnet may be used as a reference instead.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. An apparatus for tracking a position and orientation in three-dimensional space of one or more objects, the apparatus comprising:

one or more tracked sensor units, each tracked sensor unit attached to a respective one of the one or more objects and comprising one or more light sources and an inertial measurement unit, wherein the one or more light sources are configured to strobe at a particular frequency;

one or more position sensitive detector tracking devices, each position sensitive detector tracking device comprising: A) a plurality of position sensitive detector sensors combined with optical lenses that focus light from a field of view onto each position sensitive detector sensor, and B) a local inertial measurement unit, wherein the one or more position sensitive detector tracking devices are configured to discern the one or more tracked sensor units from different tracked sensor units provided on different objects to be tracked based on the particular frequency, and wherein each of the plurality of position sensitive detector sensors generates a current that is proportional to a location of a received incident light spot from the one or more light sources; and a processor configured to calculate the position and orientation of each of the one or more objects in three-dimensional space, wherein the orientation of each particular object of the one or more objects is calculated with respect to each respective one of the one or more position sensitive detector tracking devices based on: 1) orientation measurements from the inertial measurement unit of a tracked sensor unit, of the one or more tracked sensor units, attached to the particular object, and 2) orientation measurements from the local inertial measurement unit of the respective position sensitive detector tracking device, wherein in response to light emitted from the one or more light sources of the respective tracked sensor unit being focused onto each of the plurality of position sensitive detector sensors of the one or more position sensitive detector tracking devices, each of the plurality of position sensitive detector sensors measures a 2D location of the one or more light sources of the respective tracked sensor unit with respect to that position sensitive detector sensor, and the processor is configured to triangulate a 3D position of the one or more light sources of the respective tracked sensor unit based on the 2D locations measured by the plurality of position sensitive detector sensors.

2. The apparatus of claim 1, wherein the one or more light sources of each tracked sensor unit comprise one or more light emitting diodes.

3. The apparatus of claim 2, wherein the one or more light sources of each tracked sensor unit comprises a plurality of light emitting diodes arranged around an axis of the respective object to which the tracked sensor unit is attached.

4. The apparatus of claim 1, wherein each tracked sensor unit further comprises a respective processor configured to control activation of the one or more light sources and to transmit orientations measurements output by the inertial measurement unit to the processor that calculates the position and orientation of the one or more objects.

5. The apparatus of claim 1, wherein the processor comprises a respective processor embedded in each of the one or more position sensitive detector tracking devices, wherein each respective processor embedded in a position sensitive detector tracking device is configured to calculate the position and orientation of each of the one or more objects in three-dimensional space with respect to that position sensitive detector tracking device from the output of the inertial measurement unit of each tracked sensor unit and output of the plurality of position sensitive detector sensors, including orientation measurements from the local inertial measurement unit, in response to light emitted from the one or more light sources of each tracked sensor unit.

6. The apparatus of claim 1 wherein each of the inertial measurement unit and the local inertial measurement unit comprises one or more of an accelerometer, a gyroscope, or a magnetometer.

7. The apparatus of claim 1, wherein at least one of the one or more objects is a handheld ultrasound transducer, the one or more light sources of the tracked sensor unit attached to the handheld ultrasound transducer comprises a plurality of light emitting diodes arranged in a pattern around the handheld ultrasound transducer, and the one or more position sensitive detector tracking devices each comprise optical lenses of a fixed focal length and a filter configured to isolate information from a range of frequencies of the light emitting diodes.

8. The apparatus of claim 7, wherein the handheld ultrasound transducer comprises a laparoscope ultrasound transducer, and wherein a first set of inertial measurement units are positioned in a first portion of the laparoscope with an ultrasound array, the first portion being rotatable relative to a fixed second portion of the laparoscope, and a second set of inertial measurement units are positioned on the fixed second portion along with the plurality of light emitting diodes.

9. The apparatus of claim 1, wherein at least one of the one or more objects is a medical instrument, the one or more light sources of the tracked sensor unit attached to the medical instrument comprises a plurality of light emitting diodes arranged in a pattern around the medical instrument, and with the one or more position sensitive detector tracking devices each comprising an optical lenses of a fixed focal length and a filter configured to isolate information from a range of frequencies of the light emitting diodes.

10. The apparatus of claim 9, wherein the medical instrument comprises a first portion that is rotatable or articulated relative to a fixed second portion of the instrument, and wherein the tracked sensor unit attached to the medical instrument comprises a first set of inertial measurement units positioned in the first portion of the medical instrument and a second set of inertial measurement units positioned in the second portion of the medical instrument along with the plurality of light emitting diodes.

11. The apparatus of claim 1, wherein the one or more position sensitive detector tracking devices comprise a plurality of position sensitive detector tracking devices, each position sensitive detector tracking device configured to track the position of each of the one or more objects in a respective coordinate system associated with that position sensitive detector tracking device.

12. The apparatus of claim 1, wherein the one or more position sensitive detector tracking devices comprise a network of position sensitive detector tracking devices each with a tracked sensor unit attached thereto, such that each position sensitive detector tracking device in the network tracks positions of the one or more objects and positions of other position sensitive detector tracking devices in the network.

13. A method for tracking a position and orientation of one or more objects in three-dimensional space, comprising:
    receiving A) orientation measurements for each object acquired from an inertial measurement unit of a tracked sensor unit attached to that object and B) orientation measurements from a local inertial measurement unit of each respective one of a plurality of position sensitive detectors;
    acquiring, from each of the plurality of position sensitive detectors, a respective 2D location measurement of at least one light source of the tracked sensor unit attached to each object in response to light from the at least one light source being focused onto the plurality of position sensitive detectors by respective optical lenses, wherein the at least one light source is configured to strobe at a particular frequency to enable the plurality of position sensitive detectors to discern the tracked sensor unit from different tracked sensor units provided on different objects to be tracked, wherein each of the plurality of position sensitive detectors generates a current that is proportional to a location of a received incident light spot from the one or more light sources;
    triangulating a 3D position of each object with respect to a reference one of the plurality of position sensitive detectors from the respective 2D location measurements acquired from the plurality of position sensitive detectors; and
    calculating a six-dimensional pose of each object including 3D position and 3D orientation of the object with respect to the reference position sensitive detector based on the triangulated 3D position and the received orientation measurements.

14. The method of claim 13, wherein the at least one light source of the tracked sensor unit attached to each object comprises a plurality of light emitting diodes arranged around an axis of the object, and the method further comprises:
    controlling a subset of the plurality of the light emitting diodes that are facing the plurality of position sensitive detectors to turn on, wherein the subset of the plurality of the light emitting diodes that are facing the plurality of position sensitive detectors is determined based on the orientation measurements of the object acquired from the inertial measurement unit.

15. The method of claim 13, wherein acquiring, from each of the plurality of position sensitive detectors, a respective 2D location measurement of at least one light source of the tracked sensor unit attached to each object in response to light from the at least one light source being focused onto the plurality of position sensitive detectors by respective optical lenses comprises:
    tracking an intensity of light on the plurality of position sensitive detectors; and
    acquiring, from the plurality of position sensitive detectors, the respective 2D location measurements in response to the intensity of the light on the plurality of position sensitive detectors being greater than a threshold.

16. The method of claim 15, further comprising:
    transmitting an acknowledgment to the tracked sensor unit attached to each object in response to acquiring, from the plurality of position sensitive detectors, the respective 2D location measurements of at least one light source of the tracked sensor unit attached to each object.

17. An apparatus for tracking position and orientation of an ultrasound probe in 3D space, comprising:
    a tracked sensor unit attached to the ultrasound probe, the tracked sensor unit comprising a plurality of light emitting diodes arranged in a pattern around an axis of the ultrasound probe and an inertial measurement unit, wherein the one or more light sources are configured to strobe at a particular frequency; and
    a position sensitive detector tracking device comprising:
        a plurality of position sensitive detector sensors combined with optical lenses that focus light emitted from one or more of the plurality of light emitting diodes of the tracked sensor unit onto each position sensitive detector sensor, wherein the position sensitive detector tracking device is configured to discern the tracked sensor unit from different tracked sensor units provided on different ultrasound probes based on the particular frequency, wherein each of the plurality of position sensitive detectors generates a current that is proportional to a location of a received incident light spot from the one or more light sources;
        a local inertial measurement unit; and
        a processor configured to calculate the position and orientation of the ultrasound probe in three-dimensional space, wherein the orientation of the ultrasound probe is calculated with respect to the position sensitive detector tracking device based on: 1) orientation measurements from the inertial measurement unit of the tracked sensor unit; and 2) orientation measurements from the local inertial measurement unit,
        wherein in response to light emitted from the plurality of light emitting diodes of the tracked sensor unit being focused onto each of the plurality of position sensitive detector sensors of the position sensitive detector tracking device, each of the plurality of position sensitive detector sensors measures a 2D location of the plurality of light emitting diodes of the tracked sensor unit with respect to that position sensitive detector sensor, and
        the processor is configured to triangulate a 3D position of the plurality of light emitting diodes of the tracked sensor unit based on the 2D locations measured by the plurality of position sensitive detector sensors.

18. The apparatus of claim 1, wherein the one or more tracked sensor units activate the one or more light sources when information from the inertial measurement unit is sent to the one or more position sensitive detector tracking devices, and wherein only light sources that are visible to the one or more position sensitive detector tracking devices are turned on.

19. The method of claim 13, further comprising:
activating the at least one light source when information from the inertial measurement unit is sent to one of the plurality of position sensitive detectors, and wherein only light sources that are visible to the one of the plurality of position sensitive detectors are turned on.

* * * * *